United States Patent [19]
Udd et al.

[11] Patent Number: 6,144,026
[45] Date of Patent: Nov. 7, 2000

[54] FIBER OPTIC GRATING CORROSION AND CHEMICAL SENSOR

[75] Inventors: Eric Udd, Fairview, Oreg.; Eric D. Haugse, Normandy Park; Angela Trego, Richland, both of Wash.

[73] Assignees: Blue Road Research, Troutdale, Oreg.; The Boeing Company, Seattle, Wash.

[21] Appl. No.: 09/174,023

[22] Filed: Oct. 16, 1998

Related U.S. Application Data

[60] Provisional application No. 60/052,933, Oct. 17, 1997.

[51] Int. Cl.[7] ................................................. G01B 9/02
[52] U.S. Cl. ............................ 250/227.14; 250/227.18; 387/37
[58] Field of Search ..................... 250/227.14, 227.17, 250/227.18, 227.23, 231.19; 356/32, 35.5; 73/800; 385/37, 11, 12

[56] References Cited

U.S. PATENT DOCUMENTS

| | | | |
|---|---|---|---|
| 4,488,040 | 12/1984 | Rowe .................................. | 250/227.14 |
| 5,309,533 | 5/1994 | Bonniau et al. ........................... | 385/11 |
| 5,380,995 | 1/1995 | Udd et al. . | |
| 5,397,891 | 3/1995 | Udd et al. . | |
| 5,399,854 | 3/1995 | Dunphy et al. . | |
| 5,493,113 | 2/1996 | Dunphy et al. . | |
| 5,591,965 | 1/1997 | Udd . | |
| 5,646,401 | 7/1997 | Udd . | |
| 5,828,059 | 10/1998 | Udd . | |
| 5,841,131 | 11/1998 | Schroeder et al. ................. | 250/227.17 |

OTHER PUBLICATIONS

M. G. Xu, H. Geiger and J. P. Dakin, "Multiplexed Point and Stepwise Continuous Fibre Grating Based Sensors: A Practical Sensor For Structural Monitoring?" Proc. of SPIE, vol. 2294, p. 69, 1994.

M. G. Xu, J. L. Archambault, L. Reekie and J. P. Dakin "Discrimination Between Strain and Temperature Using Dual Wavelength Fibre Grating Sensors", Electronics Letters, vol. 30, p. 1085, 1994.

*Primary Examiner*—Stephone B. Allen
*Attorney, Agent, or Firm*—George W. Finch

[57] ABSTRACT

A fiber grating corrosion sensor system which includes fiber grating corrosion and/or chemical sensors formed by writing one or more fiber gratings that are transverse load sensitive so that when corrosion occurs to a transverse stress applying sleeve there over, the transverse loading is relieved. The spectral signals from the fiber grating sensors change with variations in transverse strain providing a measurement of the degree of corrosion or change in chemical content.

20 Claims, 9 Drawing Sheets

FIBER OPTIC GRATING CORROSION AND CHEMICAL SENSOR

This application claims the benefit of U.S. Provisional Application No. 60/052,933 by Eric Haugse and Eric Udd, entitled "Fiber Optic Grating Corrosion and Chemical Sensor" which was filed on Oct. 17, 1997 and contains descriptions that form a part of this invention.

BACKGROUND OF THE INVENTION

There is a need to measure corrosion on aircraft, bridges, buildings and manufacturing and process control equipment. As an example of the magnitude of this problem the U.S. Air Force estimated in 1991 that the cost of treating corrosion on its aircraft was approximately $718,000,000. The costs associated with commercial aircraft, bridges and buildings in the U.S. alone are expected to be significantly larger. To address this problem in a cost effective manner, means are needed to nondestructively test for corrosion at many key points over distances that in some cases can be hundreds of meters.

For many structural applications, the use of fiber gratings has been proposed as a method to measure strain. A great deal of work has been done investigating the usage of fiber gratings to measure axial strain and temperature. In many cases where the fiber gratings are embedded into structures, the fiber gratings are exposed to transverse strain that can result in a spectral shifts of magnitudes approaching the spectral shifts caused by longitudinal strains and/or temperature shifts. E. Udd, in U.S. Pat. No. 5,591,965, which issued Jan. 7, 1997, describes a three axis strain and temperature fiber grating sensor formed by writing two overlaid fiber gratings onto a birefringent fiber. As an example wavelengths of the fiber gratings can be written at 1.300 and 1.550 microns. By writing onto the highly birefringent fiber four gratings are established. In the case of about a two millimeter beat length at 630 nm they would be at 1300.0, 1300.6, 1550.0 and 1550.8 nm. The birefringent axes are well defined so that transverse strain can be measured along with longitudinal strain and temperature through four equations with four unknowns.

Further improvements in the measurement of transverse strain were made by E. Udd in patent application U.S. Ser. No. 08/707,861 entitled, "Transverse Strain Measurements Using Fiber Optic Grating Based Sensors", filed Sep. 9, 1996 now U.S. Pat. No. 5,828,059. These patent applications describe transverse fiber grating strain sensors that have improved transverse strain sensitivity and greatly reduced thermal sensitivity.

Fiber optic corrosion sensors that have been proposed often rely on spectral analysis of chemical analytes placed at the end or in the evanescent field of an optical fiber. When corrosion is present the spectral signal changes. The corrosion sensors based on chemically induced changes in the spectrum are difficult to multiplex, expensive to implement and are subject to erroneous signals due to the presence of chemical contaminants that do not represent corrosion, but induce spurious signals.

What is needed is a corrosion sensor that is compatible with a fiber grating strain sensor system usable for structural health monitoring, which also serves to provide necessary state of corrosion information.

SUMMARY OF THE INVENTION

In the present invention, corrosion and chemical sensor systems are formed by using one or more fiber gratings whose transverse strains vary with adjacent states of corrosion or chemical attack. These transverse strain forces may be created by encapsulating a fiber grating into a sleeve that is crushed, heat treated, or elastically expanded or contracted to cause an initial transverse loading or by using two half cylinders on opposite sides of a fiber grating inside some sort of force applying device. Normally, the half cylinders are placed in a heat expanded sleeve of metal or press fit sleeve. When the sleeve cools and contracts, it forces the half cylinders together so they transverse load the fiber grating there between. Materials, such as Nitinol, that have non-linear shape changes with temperature, can also be used. When a fiber is transverse loaded by these mechanisms, a peak to peak separation of the reflected and transmitted spectral profiles of the fiber grating results. As corrosion or other chemical reaction of the sleeve occurs, the transverse strain is relieved and the peak to peak spectral separation changes allowing a measurement of corrosion. Different metals and stretchable plastics can be used as the sleeve material to support the measurement of a variety of corrosion events.

The performance of the fiber grating corrosion sensor depends upon the type of transverse fiber grating sensor selected. In particular, transverse fiber grating sensors can be selected that have reduced thermal sensitivity, or in some cases to allow the simultaneous measurement of transverse stress and temperature. Because the transversely loaded fiber grating corrosion sensors are compatible with similar fiber grating based strain sensor systems being used for structural monitoring, they are compatible with strain sensor demodulation equipment and can become interchangeable elements of an overall structural health monitoring system.

Therefore it is an object of the invention to provide a fiber grating corrosion sensing system that is compatible with existing structural strain measurement systems, thereby reducing overall cost and complexity.

Another object is to provide a corrosion sensor that can be easily constructed to sense a variety of corrosion events.

Another object of the invention is to provide a corrosion sensor with reduced temperature sensitivity.

Another object of the invention is to provide a corrosion sensor that can measure environmental effects, such as temperature or pressure, in addition to corrosion.

These and other objects and advantages of the present invention will become apparent to those skilled in the art after considering the following detailed specification including the drawings wherein:

DETAILED DESCRIPTION OF THE INVENTION

Figure 1:
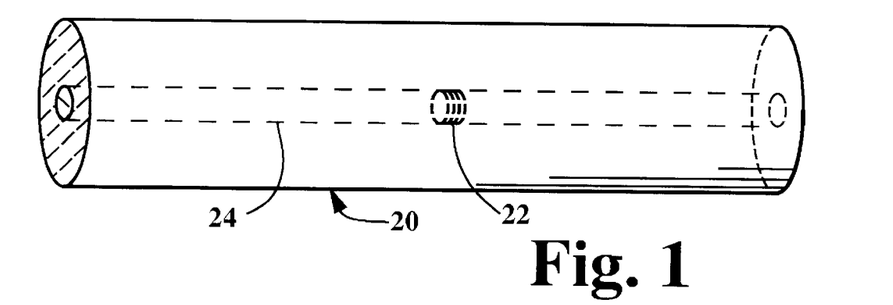
FIG. 1 is a perspective view of a prior art fiber grating sensor based on writing a single grating onto optical fiber.
Figure 2A:
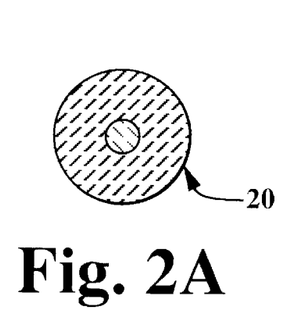
FIGS. 2A, 2B, and 2C are exaggerated cross-sectional views of the sensor of FIG. 1 with no, a small amount, and a large amount of stress being applied transversely thereto respectively.
Figure 2B:
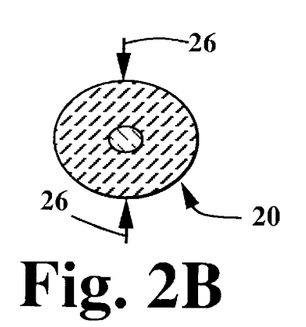
Figure 2C:
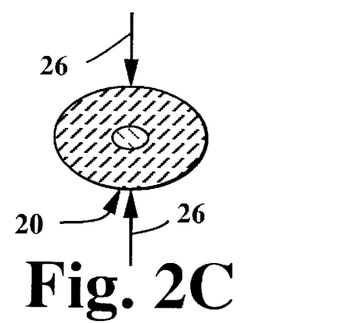
Figure 3A:
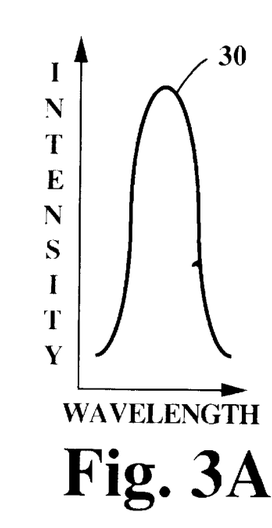
FIGS. 3A, 3B, and 3C are intensity vs. wavelength diagrams of the spectral reflective output from the sensor of FIGS. 2A, 2B, and 2C with increasing transverse strain applied to the sensor.
Figure 3B:
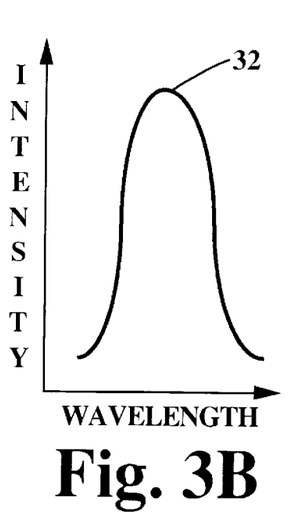
Figure 3C:
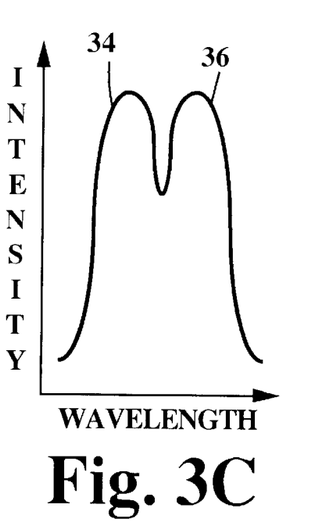

FIG. 1 shows a prior art fiber grating sensor 20 based on writing a single grating 22 onto optical fiber 24, while FIGS. 2A, 2B, and 2C show, in exaggerated form, what happens to the sensor 20 when transverse stress (shown by arrows 26) is applied thereto. The spectral reflective outputs from the sensor 20 with none, a small amount, and a large amount of transverse stress are shown in FIGS. 3A, 3B, and 3C respectively. The unstrained sensor 20 reflects a spectrum consisting of a single peak 30. As transverse stress is applied to the sensor 20, it reflects a spectrum consisting of a broader peak 32 and as the stress increases, the sensor 20 reflects a spectrum consisting of split peaks 34 and 36.

Figure 4:
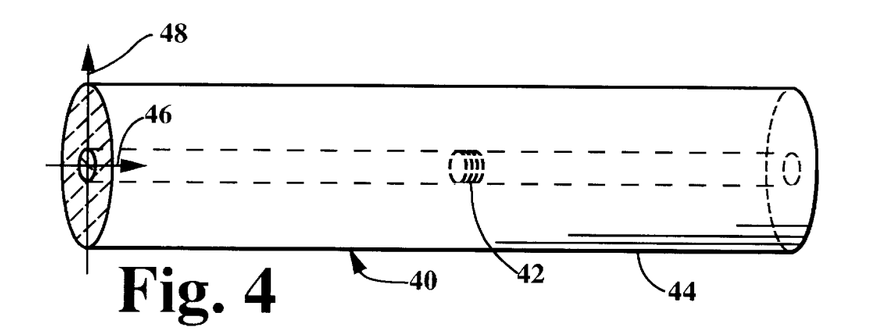
FIG. 4 is a perspective view of a multiaxis fiber grating sensor based on writing a single fiber grating onto birefringent optical fiber.

FIG. 4 shows a fiber grating sensor 40 based on writing a single grating 42 onto a length of birefringent optical fiber 44. This sensor 40 may be used to measure transverse as well as axial strain. The birefringent optical fiber 44 of the fiber grating sensor 40 may be polarization preserving optical fiber with different indices of refraction along the axes 46 and 48.

Figure 5A:
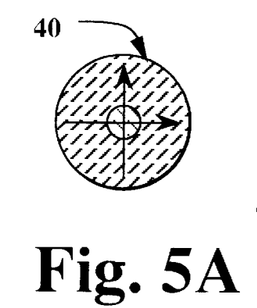
FIGS. 5A, 5B, and 5C are exaggerated cross-sectional views of the sensor of FIG. 4 with no, a small amount, and a large amount of stress being applied transversely thereto respectively.
Figure 5B:
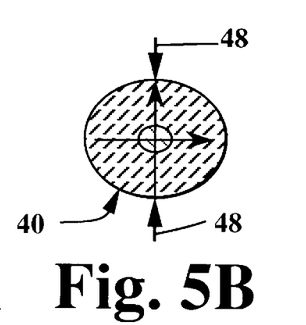
Figure 5C:
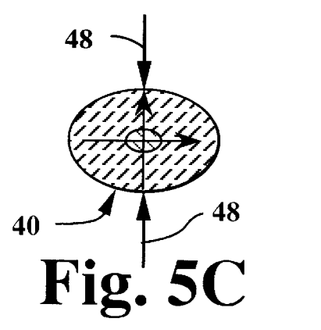
Figure 6A:
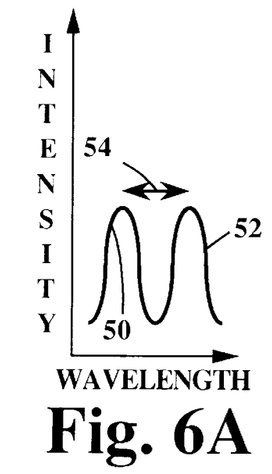
FIGS. 6A, 6B, and 6C are intensity vs. wavelength diagrams of the spectral reflective output from the sensor of FIGS. 5A, 5B, and 5C with increasing transverse strain applied to the sensor.
Figure 6B:
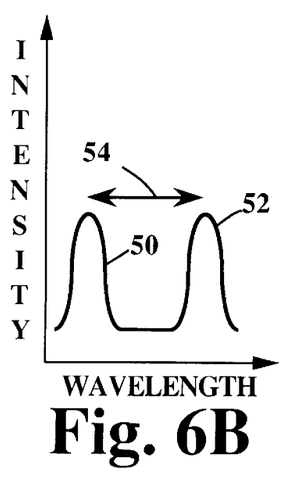
Figure 6C:
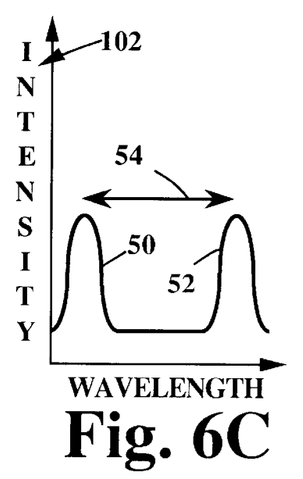

FIGS. 5A, 5B, and 5C show, in exaggerated form, what happens to the sensor 40 when transverse stress (shown by arrows 48) is applied thereto. The spectral reflective outputs from the sensor 40 with none, a small amount, and a large amount of transverse stress are shown in FIGS. 6A, 6B, and 6C respectively. The unstrained sensor 40 reflects a spectrum consisting of dual peaks 50 and 52 with a separation 54 there between. As the transverse strain of the sensor 40 increases, the dual peaks 50 and 52 increase in separation 54.

Figure 7:
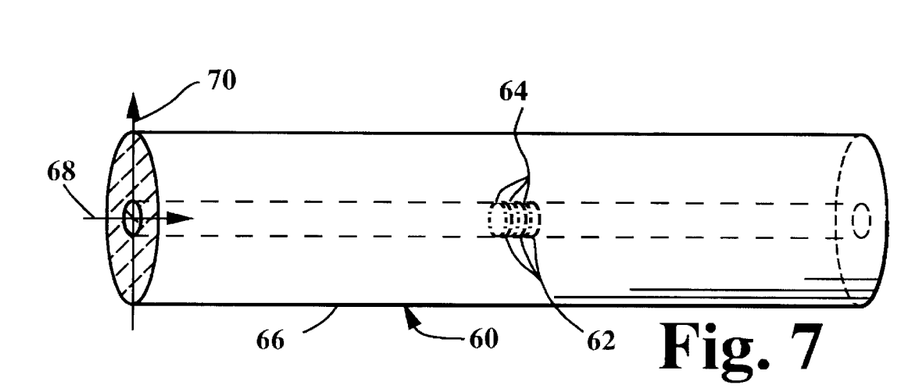
FIG. 7 is a perspective view of a multiaxis fiber sensor based on writing two fiber gratings at different wavelengths onto birefringent optical fiber.

FIG. 7 shows a prior art transverse fiber grating sensor 60 based on dual overlaid fiber gratings 62 and 64 written onto birefringent optical fiber 66 as described by E. Udd in "Advanced Strain Measurement Applications of Fiber Optic Grating Sensors", Proceedings of SPIE, volume 2872, p. 18–23, 1996 and C. M. Lawrence, D. V. Nelson and E. Udd in "Multi-Parameter Sensing with Bragg Gratings", Proceedings of SPIE, volume 2872, p. 24–31, 1996 as well as by E. Udd in U.S. Pat. No. 5,591,965, Jan. 7, 1997. This fiber sensor 60 may be used to measure transverse as well as axial strain as described in the above references. The multiaxis fiber grating strain sensor 60 is comprised of the length of birefringent optical fiber 66, which may be polarization preserving optical fiber with different indices of refraction along the axes 68 and 70. When dual overlaid fiber gratings 62 and 64 are written onto the birefringent fiber 66, four distinct spectral peaks result. Changes in the wavelength of these four peaks can then be used to solve for multiple axes of strain and temperature.

Figure 8:
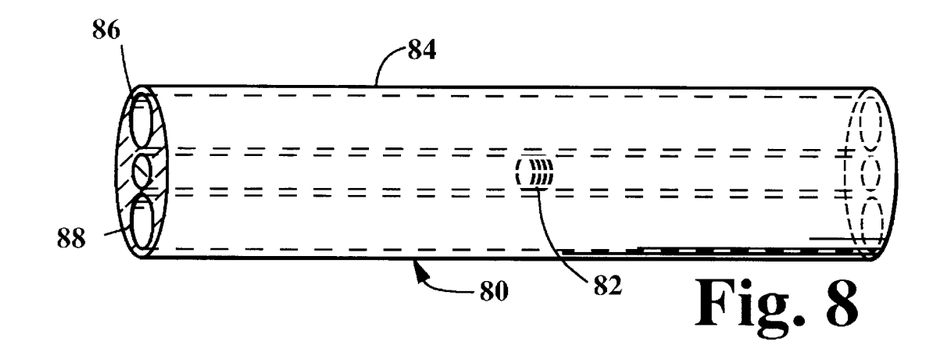
FIG. 8 is a perspective view of a transverse fiber grating strain sensor formed by writing a fiber grating onto sidehole optical fiber.

FIG. 8 shows a transverse fiber grating strain sensor 80 formed by writing a fiber grating 82 onto optical fiber 84 with sideholes 86 and 88. The transverse fiber grating strain sensor 80 will reflect spectrums similar to those shown in FIGS. 2A, 2B, and 2C when subject to transverse strain, but the sideholes 86 and 88 make the sensor 80 more sensitive to transverse strain.

Figure 9:
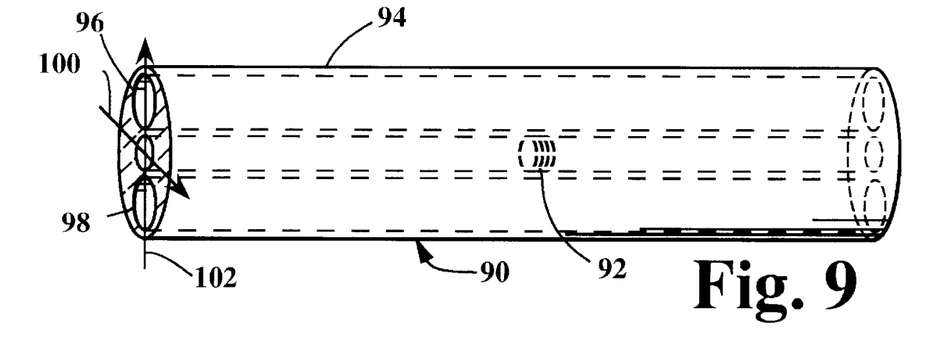
FIG. 9 is a perspective view of a multiaxis fiber grating sensor formed by writing a fiber grating onto birefringent sidehole optical fiber.

FIG. 9 shows a multiaxis fiber grating sensor 90 formed by writing a fiber grating 92 onto birefringent sidehole optical fiber 94. The sideholes 96 and 98 and the fiber 94 may have different indices of refraction along the axes 100 and 102, which along with the sideholes 96 and 98 may make the sensor more sensitive to transverse strain. The sensor 90 will reflect spectrums similar to those shown in FIGS. 5A, 5B, and 5C when subject to transverse strain.

Figure 10:
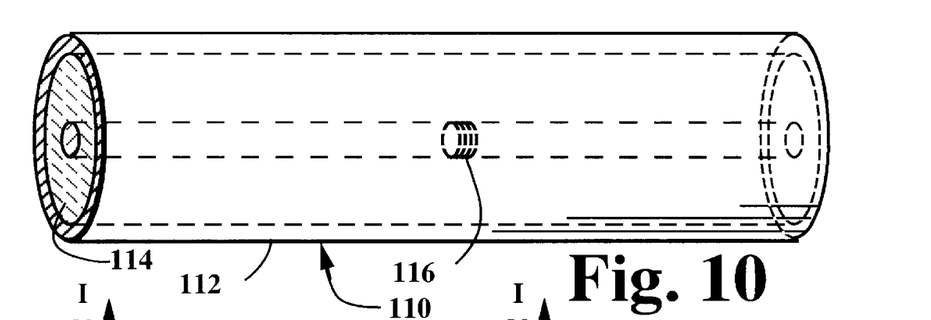
FIG. 10 is a perspective view of a fiber grating strain sensor with a metallic sleeve or other corroding material placed over it and crushed to apply transverse stress.
Figures 11A, 11B, 12, 13A, 13B:
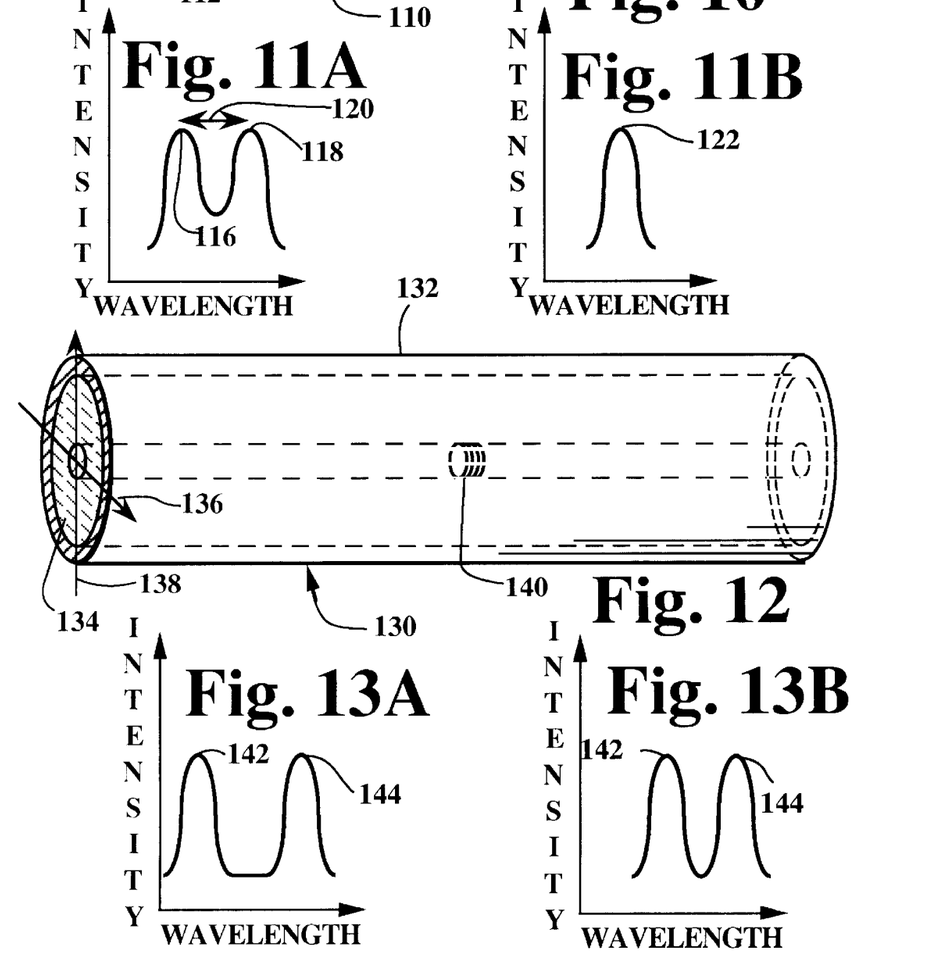
FIGS. 11A and 11B, are intensity vs. wavelength diagrams of the spectral reflective output from the sensor of FIG. 10 before and after the transverse stressing sleeve has corroded.
FIG. 12 illustrates a multiaxis fiber grating sensor with a metallic sleeve or other corroding material placed over it and crushed to apply transverse stress.
FIGS. 13A and 13B, are intensity vs. wavelength diagrams of the spectral reflective output from the sensor of FIG. 12 before and after the transverse stressing sleeve has corroded.

FIG. 10 shows a fiber grating strain sensor 110 with a metallic sleeve 112 or other corroding material placed over a length of optical fiber 114 onto which a grating 116 has been written. The sleeve 112 may be crushed once it is placed on the fiber 114 to create residual transverse stress that strains the fiber 114, or other means of sleeve deformation may be employed to create the residual transverse stress. FIG. 11A shows the spectral reflective output with two peaks 116 and 118 from the sensor 110 of FIG. 10 with the sleeve 114 applying transverse stress thereto. As the sleeve is corroded, the fiber 114 becomes less and less strained and the gap 120 between the peaks 116 and 118 also becomes less and less, until when the sleeve 112 is no longer able to apply transverse stress, the reflected spectrum is reduced a single peak 122. Therefore, the gap 120 becomes a measure of the degree of corrosion that has taken place.

FIG. 12 shows a multiaxis fiber grating sensor 130 with a prestressing metallic sleeve 132 or other corroding material placed over a length of birefringent optical fiber 134, which may have different indices of refraction along the axes 136 and 138. A single grating 140 is written onto this length of birefringent optical fiber 134. FIGS. 13A and 13B show the spectral reflective output from the sensor 130 of FIG. 12, both when the sleeve 132 of the sensor 130 is in an uncorroded state and a corroded state. Note that the dual peaks 142 and 144 of reflected spectrum move closer together as the sleeve corrodes, thus becoming a measure of the degree of corrosion that has taken place.

Figure 14:
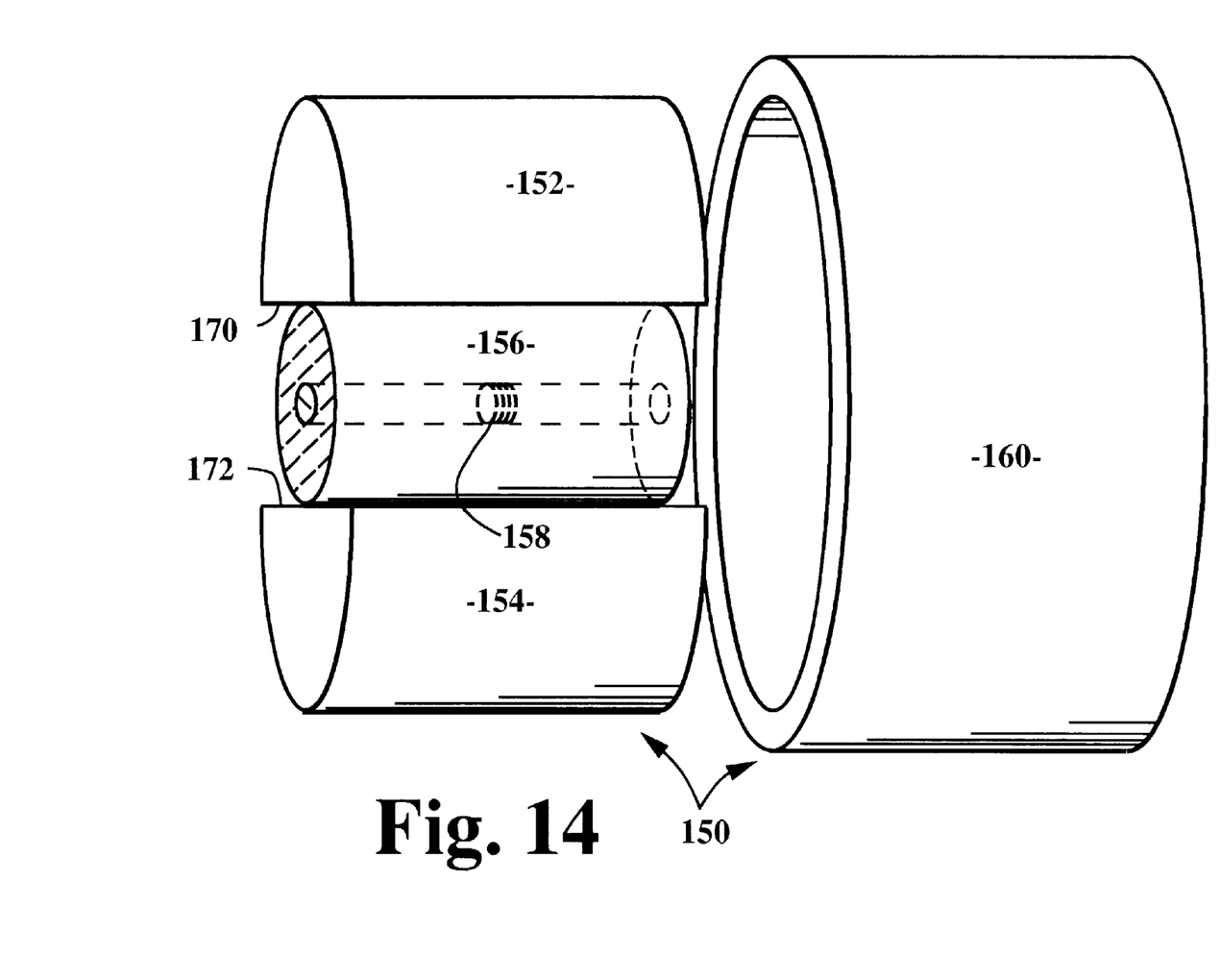
FIG. 14 is perspective exploded view illustrating the assembly of a transversely strained fiber grating corrosion sensor positioned between two cylindrical half shells that are preloaded against the sensor by placing a heat expanded or press fit sleeve over them.
Figure 15A:
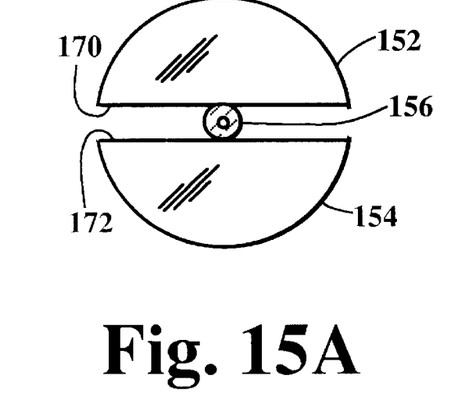
FIG. 15A is cross section of the fiber grating sensor between the cylindrical halves used to exert transverse force of FIG. 14.
Figure 15B:
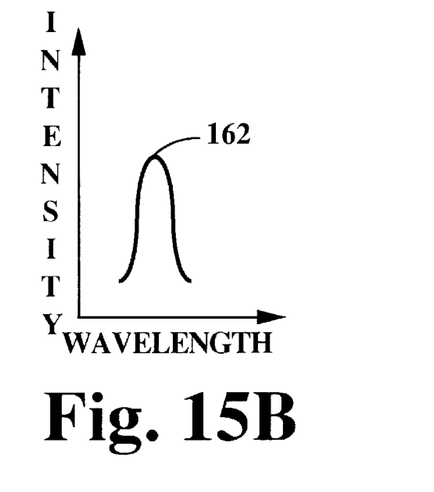
FIG. 15B is an intensity vs. wavelength diagram of the spectral reflective output from the sensor of FIG. 15A before a transverse stressing sleeve is positioned there about.

FIG. 14 shows the assembly of a transversely strained fiber grating corrosion sensor 150 formed by two cylindrical half shells 152 and 154 that are preloaded against an optical fiber 156 with a grating 158 written thereon, by placing a heat expanded sleeve 160 over them. As shown in FIG. 15A, the optical fiber 156 and fiber grating 158 are placed between the two cylindrical half shells 152 and 154. Without transverse strain, the spectral reflection, as shown in FIG. 15B has only one peak 162. Transverse strain is then induced on the optical fiber 156 and fiber grating 158 via the half shells 152 and 154 by heating the sleeve 160, placing it over the half shells 152 and 154 and allowing the sleeve 160 to cool and constrict. The fiber grating sensor 150 could include of a single element fiber grating 158, such as that described in association with FIG. 1, a single or dual element fiber grating sensor written onto birefringent fiber similar to that described in association with FIGS. 4 and 7 respectively, or sidehole fiber grating transverse strain sensors similar to those shown in FIGS. 8 and 9. In the case of birefringent and sidehole based fiber grating transverse strain sensors, it is desirable that the principle stain axes 164 be aligned to the transverse strain applied by the crushed metallic sleeve 112 in the case of FIG. 10, or the plane of the two cylindrical half shells 152 and 154 of the arrangement shown in FIG. 16A. That is the most sensitive axes of the fiber grating transverse strain sensors should be aligned to the axes along which corrosion will induce the maximum change in transverse strain.

Figure 16A:
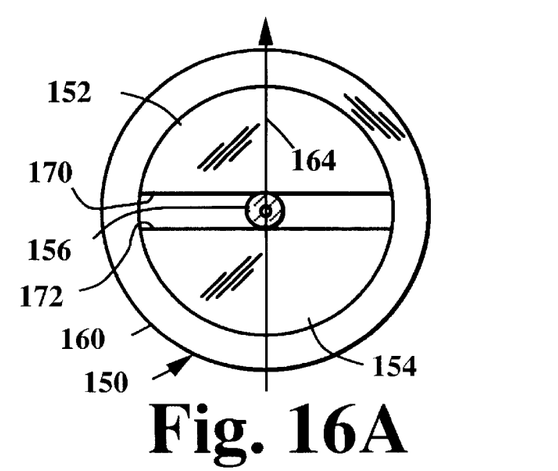
FIG. 16A is cross section of the fiber grating sensor between the cylindrical halves used to exert transverse force with a transverse stressing sleeve positioned there about.
Figure 16B:
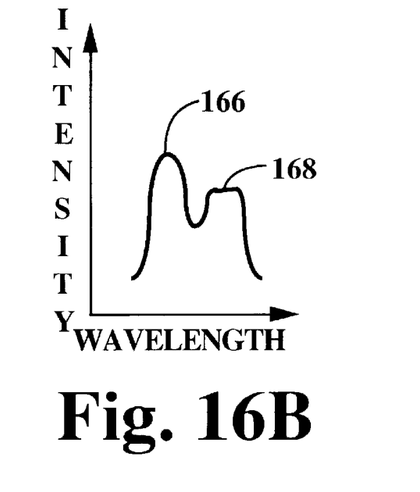
FIG. 16B is an intensity vs. wavelength diagram of the spectral reflective output from the sensor of FIG. 16A.

FIG. 16B shows the spectral reflective output from the sensor 150 in FIG. 16A after the sleeve 160 is placed over the two cylindrical half shells 152 and 154. The fiber grating sensor 150 is in a transverse strained state and reflects a spectrum containing split peaks 166 and 168 whose spacing inversely represents the state of corrosion of the sleeve 160. The distortion of the peak 168 is caused by nonuniform transverse strain loading across the axis along which transverse force is being applied. The non-uniformity is partly because the flat surfaces 170 and 172 of the two cylindrical half shells 152 and 154, and partly because of small roughness of the flat surfaces 170 and 172. These transverse strain gradients result in a spreading and distortion of the loaded peak and the interpretation of the gradients can aid in assessing the degree of corrosion.

Figure 17:
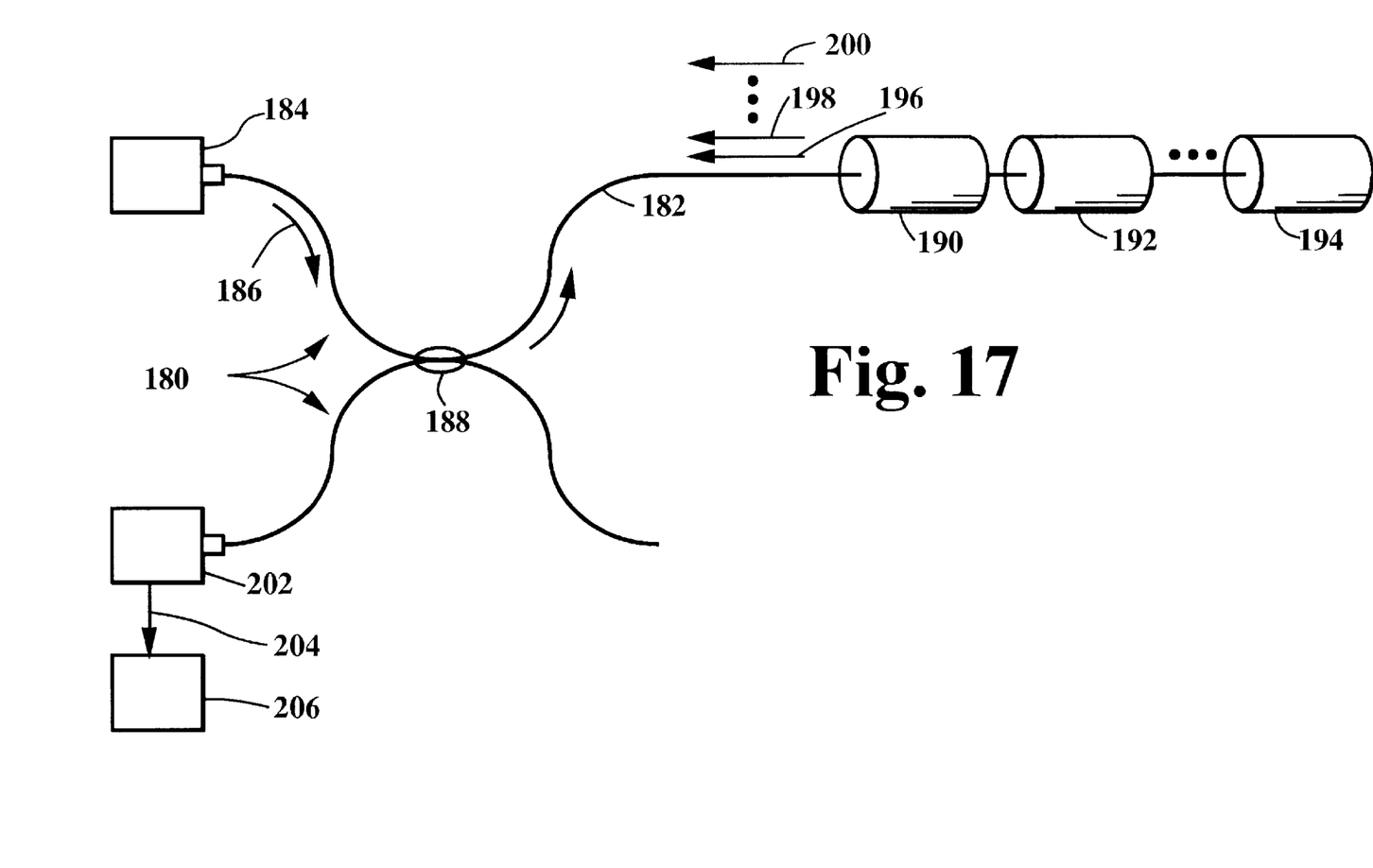
FIG. 17 is a diagram illustrating how fiber grating corrosion sensors may be multiplexed in a single fiber.

FIG. 17 shows a system 180 where one or more of the types of the previously described fiber grating corrosion sensors may be multiplexed in a single fiber 182. A broadband light source 184, such as an edge light emitting diode, sends a broadband spectrum 186 to a beamsplitter 188 and is directed to the corrosion sensors 190, 192 and 194, each containing a fiber grating sensor with a grating written at wavelength $\lambda 1$, $\lambda 2$, and $\lambda n$ respectively where n is the wavelength of the grating written onto the fiber grating sensor of the last corrosion sensor in the line. The corrosion sensors 190, 192 and 194 reflect spectrums 196, 198, and 200 respectively back to the beamsplitter 188 where they are directed to a demodulator 202, which can demodulate the spectra, such as an optical spectrum analyzer, a fiber Fabry Perot scanning etalon, or an acoustooptic tunable filter. The electrical output 204 from the demodulator 202 is then directed toward a data recorder 206.

Figure 18:
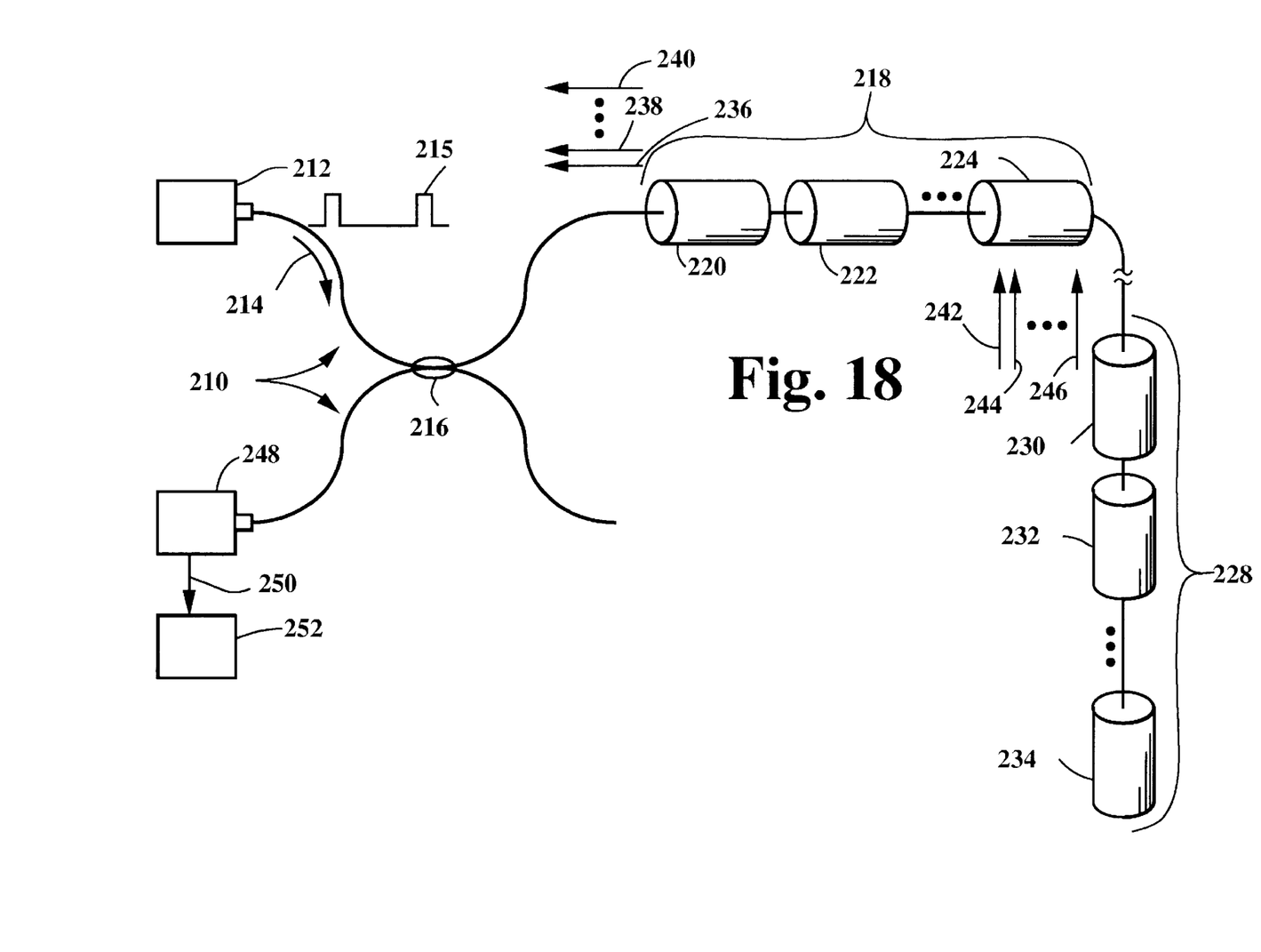
FIG. 18 is a diagram showing how time and wavelength division multiplexing may be combined to multiplex a large number of corrosion sensors.

FIG. 18 shows a system 210 where time and wavelength division multiplexing may be combined to multiplex a large number of corrosion sensors. A broadband light source 212, such as an edge light emitting diode, sends a light beam 214 with a broadband spectrum in pulses 215 to a beamsplitter 216. The light beam 214 is than split and directed to a set 218 of corrosion sensors, including corrosion sensors 220, 222, and 224, each containing a fiber grating sensor with a grating written at wavelength $\lambda 1$, $\lambda 2$, and $\lambda n$ respectively, where n is the wavelength of the grating written onto the fiber grating sensor of the last corrosion sensor in the set 218. Each pulse 215 then continues along the fiber optic line 226 a significant distance to cause a measurable time delay to another set 228 of corrosion sensors 230, 232, and 234. The set of corrosion sensors 230, 232, and 234 each contain a grating written at wavelength $\lambda 1$, $\lambda 2$, and $\lambda n$ respectively where n is the wavelength of the grating written onto the fiber grating sensor of the last corrosion sensor in the set 228. The corrosion sensors 220, 222, and 224 reflect spectrums 236, 238, and 240 respectively and corrosion sensors 230, 232, and 234 reflect spectrums 242, 244, and 246 respectively, back to the beamsplitter 216, where they are directed to a demodulator 248, which can demodulate the spectra such as an optical spectrum analyzer, a fiber Fabry Perot scanning etalon, or an acoustooptic tunable filter. The electrical output 250 from the demodulator 248 is then directed toward a data recorder 252.

Figure 19:
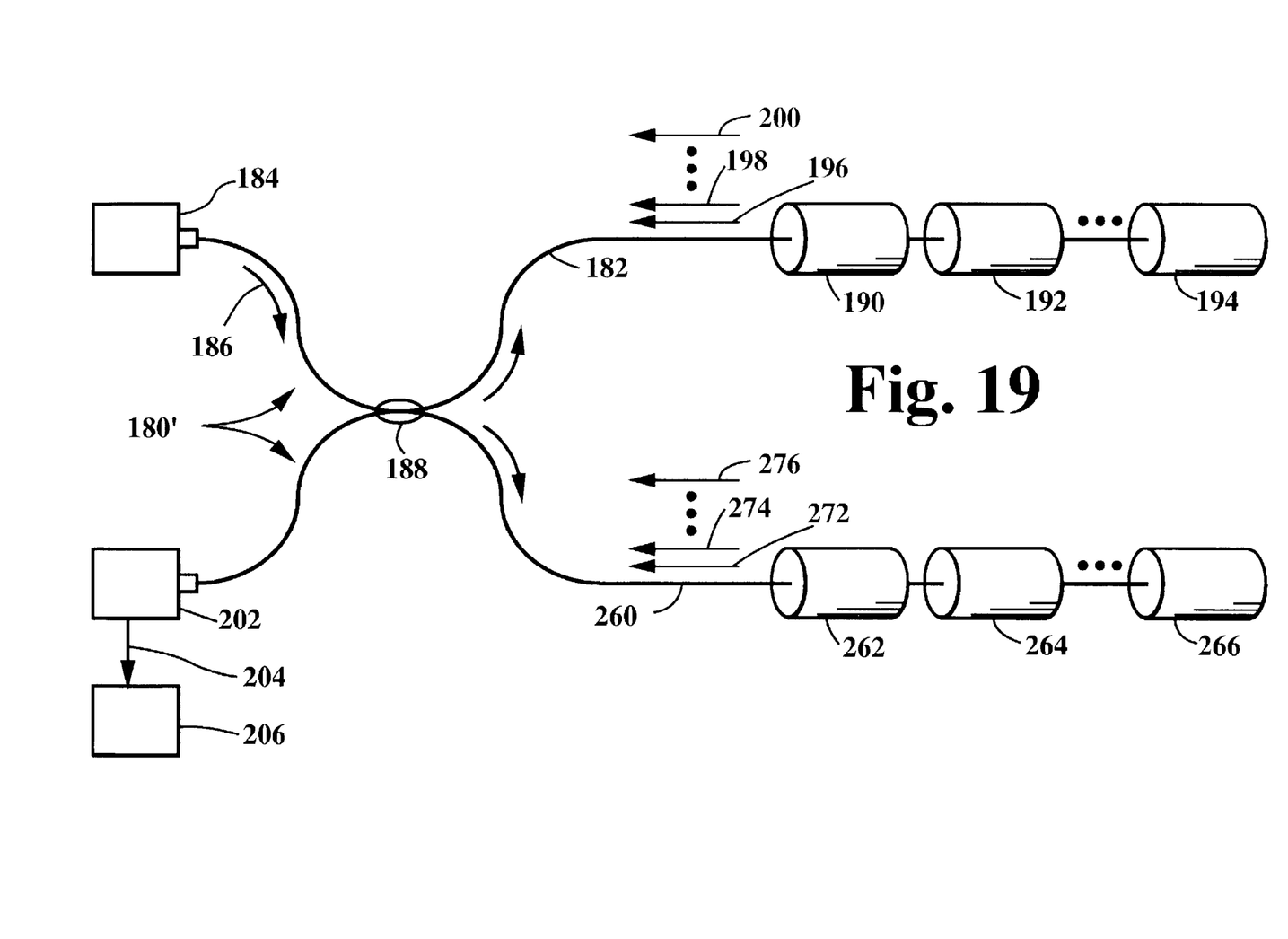
FIG. 19 is an illustration of how fiber grating sensors may be multiplexed in line to perform a series of functions that may include axial strain, transverse strain, corrosion, hydrogen presence, ice and pressure.

FIG. 19 is a modified system 180' that shows how fiber grating sensors may be multiplexed in line to perform a series of functions that may include axial strain, transverse strain, corrosion, hydrogen presence, ice and pressure. The broadband light source 184 sends the broadband spectrum 186 to the beamsplitter 188 and is split among two fiber optic lines 182 and 260. The fiber grating based sensors 190, 192, and 194 on the fiber optic line 182 may be axial strain and temperature sensors, a transverse strain sensor, a corrosion sensor, and a hydrogen presence sensor. Fiber optic line 260 may contain fiber grating based sensors 262, 264, and 266, such as an ice presence sensor, a pressure sensor, another corrosion sensor, and a multiaxis strain sensor. The fiber grating based sensors along fiber optic lines 182 and 260 could reflect spectra 196, 198, and 200, and 272, 274, and 276, each with unique wavelengths to distinguish the separate sensors. These reflected spectra are directed back to the beamsplitter 188 and toward the demodulator 202. The electrical output 204 from the demodulator 202 is then directed toward the data recorder 206.

Thus there has been shown and described a novel fiber grating corrosion sensor system that may be multiplexed via standard wavelength division and time division multiplexing as well as by optical switches which fulfill all the objects and advantages sought therefor. Many changes, modifications, alterations and other uses and applications which do not depart from the spirit and scope of the invention are deemed to be covered by the invention which is limited only by the claims that follow:

What is claimed is:

1. A fiber grating sensor including:
   a fiber grating element, having:
      a fiber grating therein; and
   a covering positioned about said fiber grating element to apply transverse stress to said fiber grating, said covering being constructed from material that weakens to reduce the transverse stress applied to said fiber grating when subjected to an environment whose effect is to be sensed.

2. The fiber grating sensor as defined in claim 1 wherein said fiber grating element includes:
   a birefringent fiber with said fiber grating written into said birefringent fiber.

3. The fiber grating sensor as defined in claim 1 wherein said fiber grating includes:
   a first fiber grating having a first spacing; and
   a second fiber grating having a second spacing, and wherein said fiber grating element includes:
      a birefringent fiber with said first and second fiber gratings written into said birefringent fiber at essentially the same place.

4. The fiber grating sensor as defined in claim 1 wherein said fiber grating includes:
   a first fiber grating having a first spacing; and
   a second fiber grating having a second spacing, and wherein said first and second fiber gratings are written into said fiber grating element at essentially the same place.

5. The fiber grating sensor as defined in claim 1 wherein said fiber grating element includes:
   a sidehole optical fiber with said fiber grating written into said sidehole optical fiber.

6. The fiber grating sensor as defined in claim 1 wherein said fiber grating includes:
   a first fiber grating having a first spacing; and
   a second fiber grating having a second spacing, and wherein said fiber grating element includes:
      a sidehole optical fiber with said first and second fiber gratings written into said sidehole optical fiber at essentially the same place.

7. The fiber grating sensor as defined in claim 1 wherein said fiber grating includes:
   a first fiber grating having a first spacing; and
   a second fiber grating having a second spacing, and wherein said fiber grating element includes:
      a birefrigent sidehole optical fiber with said first and second fiber gratings written into said birefrigent sidehole optical fiber at essentially the same place.

8. The fiber grating sensor as defined in claim 1 wherein said fiber grating element includes:
   a first semi-cylindrical element positioned between said covering and said fiber grating; and
   a second semi-cylindrical element positioned between said covering and said fiber grating opposite said first semi-cylindrical element, whereby said covering forces said first and second semi-cylindrical elements together about said fiber grating.

9. The fiber grating sensor as defined in claim 8 wherein said fiber grating element includes:
   a birefringent fiber with said fiber grating written into said birefringent fiber.

10. The fiber grating sensor as defined in claim 8 wherein said fiber grating includes:
    a first fiber grating having a first spacing; and
    a second fiber grating having a second spacing, and wherein said fiber grating element includes:
       a birefringent fiber with said first and second fiber gratings written into said birefringent fiber at essentially the same place.

11. The fiber grating sensor as defined in claim 8 wherein said fiber grating includes:
    a first fiber grating having a first spacing; and
    a second fiber grating having a second spacing, and wherein said first and second fiber gratings are written into said fiber grating element at essentially the same place.

12. The fiber grating sensor as defined in claim 8 wherein said fiber grating element includes:
    a sidehole optical fiber with said fiber grating written into said sidehole optical fiber.

13. The fiber grating sensor as defined in claim 8 wherein said fiber grating includes:
    a first fiber grating having a first spacing; and
    a second fiber grating having a second spacing, and wherein said fiber grating element includes:
       a sidehole optical fiber with said first and second fiber gratings written into said sidehole optical fiber at essentially the same place.

14. The fiber grating sensor as defined in claim 8 wherein said fiber grating includes:
    a first fiber grating having a first spacing; and
    a second fiber grating having a second spacing, and wherein said fiber grating element includes:
       a birefrigent sidehole optical fiber with said first and second fiber gratings written into said birefrigent sidehole optical fiber at essentially the same place.

15. A fiber grating sensor system including:
    a first fiber grating element, having:
       a first fiber grating therein; and
    a covering positioned about said first fiber grating element to apply transverse stress to said first fiber grating, said covering being constructed from material that weakens to reduce the transverse stress applied to said first fiber grating when subjected to an environment whose effect is to be sensed.

16. The fiber grating sensor system as defined in claim 15 further including:
    a light source for producing a first light beam;
    a beamsplitter operatively connected to said light source and said first fiber grating element to transmit the first light beam to said first fiber grating; and
    detector means to monitor changes in reflection spectra of said first light beam from said first fiber grating, whereby changes in said reflection spectra indicate reduced transverse stress applied to said first fiber grating.

17. The fiber grating sensor system as defined in claim 16 further including:
    a second fiber grating element operatively connected to said beamsplitter to receive said first light beam, said detector means also monitoring reflection spectra of said first light beam from said second fiber grating, the reflection spectra from said second fiber grating being a measure of axial strain and temperature, transverse strain, corrosion, hydrogen presence, ice presence, pressure, or multiaxis strain.

18. The fiber grating sensor system as defined in claim 17 wherein said light source produce the first light beam in a series of spaced pulses, and wherein said first and second fiber grating elements are spaced from each other further than half the distance light can travel during the length of each pulse.

19. The fiber grating sensor system as defined in claim 16 wherein said first fiber grating element includes:
   a birefringent fiber with said first fiber grating written into said birefringent fiber.

20. The fiber grating corrosion sensor as defined in claim 16 wherein said first fiber grating has a first spacing and wherein said first fiber grating also includes:
   a second fiber grating having a second spacing, and wherein said first fiber grating element includes an optical fiber chosen from the group consisting of
   a birefringent fiber; and
   a sidehole optical fiber.

* * * * *